United States Patent [19]

Ekins

[11] Patent Number: 5,432,099
[45] Date of Patent: Jul. 11, 1995

[54] DETERMINATION OF AMBIENT CONCENTATION OF SEVERAL ANALYTES

[75] Inventor: Roger P. Ekins, London, Great Britain

[73] Assignee: Multilyte Limited, United Kingdom

[21] Appl. No.: 984,264

[22] Filed: Dec. 1, 1992

Related U.S. Application Data

[63] Continuation of Ser. No. 460,878, filed as PCT/GB88/00649, Aug. 5, 1988.

[30] Foreign Application Priority Data

Feb. 10, 1988 [GB] United Kingdom ............... 8803000

[51] Int. Cl.$^6$ ............... G01N 33/543; G01N 33/537; G01N 33/533
[52] U.S. Cl. ............... 436/518; 435/7.1; 435/7.92; 435/973; 436/501; 436/517
[58] Field of Search ............... 435/7.1, 7.92, 973; 436/501, 517, 518

[56] References Cited

U.S. PATENT DOCUMENTS 4,591,570 5/1986 Chang ............... 436/518
5,096,807 3/1992 Leaback ............... 435/6

FOREIGN PATENT DOCUMENTS 8401031 5/1984 WIPO ............... G01N 33/54

OTHER PUBLICATIONS

Ekins et al., "Multianalyte testing", Clin Chem. 39: 369–370 (1992).
Dudley et al., "Guidelines for Immunoassay Data Processing," Clin. Chem. 31(1264–1271) (1985).

Primary Examiner—Christine M. Nucker
Assistant Examiner—M. P. Woodward
Attorney, Agent, or Firm—Dann, Dorfman, Herrell and Skillman

[57] ABSTRACT

A method for determining the ambient concentrations of a plurality of analytes in a liquid sample of volume V liters, comprises loading a plurality of different binding agents, each being capable of binding specifically and reversibly an analyte of interest onto a support means at a plurality of spaced apart locations such that not more than 0.1 V/K moles of each binding agent are present at any location, where k liters/mole is the equilibrium constant of each such binding agent;

contracting the loaded support means with the sample to be analyzed, such that each of the spaced apart locations is contacted in the same operation with the sample, the amount of sample liquid being such that only an insignificant proportion of any analyte present in the sample becomes bound to the binding agent specific for it, and measuring a parameter representative of the fractional occupancy by the analytes of the binding agents at the spaced apart locations by a competitive or non-competitive assay technique, using a labelled site-recognition reagent for each binding agent capable of recognizing either the unfilled binding sites or the filled binding sites on the binding agent, which enables the amount of said reagent in the particular location to be measured. A device and kit for use in the method are also provided.

17 Claims, 1 Drawing Sheet

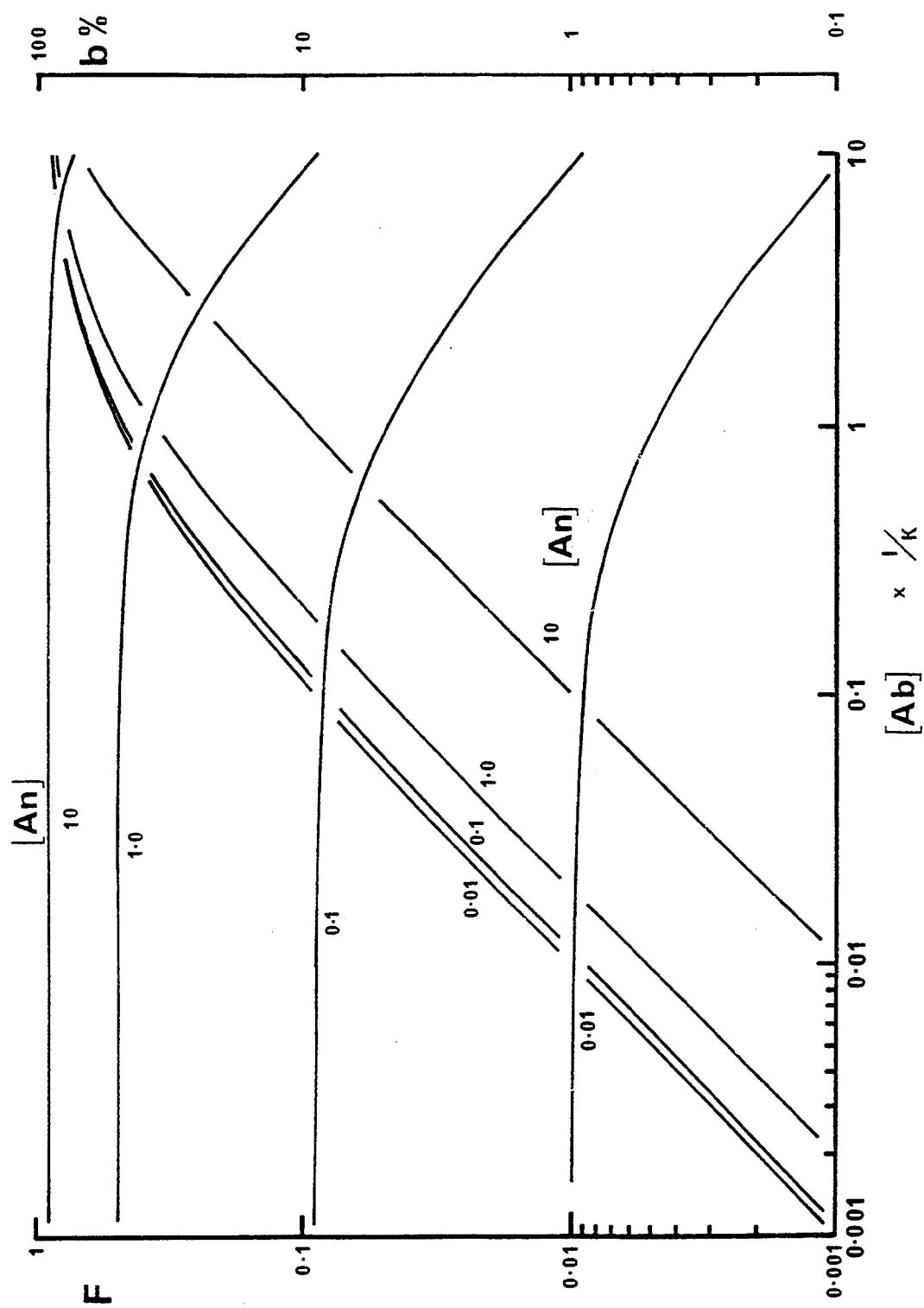

DETERMINATION OF AMBIENT CONCENTATION OF SEVERAL ANALYTES

This is a continuation of co-pending application Ser. No. 07/460,878, filed as PCT/GB88/00649, Aug. 5, 1988.

FIELD OF THE INVENTION

The present invention relates to the determination of ambient analyte concentrations in liquids, for example the determination of analytes such as hormones, proteins and other naturally occurring or artificially present substances in biological liquids such as body fluids.

BACKGROUND OF THE INVENTION

I have proposed in International Patent Application WO84/01031 to measure the concentration of an analyte in a fluid by contacting the fluid with a trace amount of a binding agent such as an antibody specific for the analyte in the sense that it reversibly binds the analyte but not other components of the fluid, determining a quantity representative of the proportional occupancy of binding sites on the binding agent and estimating from that quantity the analyte concentration. In that application I point out that, provided that the amount of binding agent is sufficiently low that its introduction into the fluid causes no significant diminution of the concentration of ambient (unbound) analyte, the fractional occupancy of the binding sites on the binding agent by the analyte is effectively independent of the absolute volume of the fluid and of the absolute amount of binding agent, i,e. independent within the limits of error usually associated with the measurement of fractional occupancy. In such circumstances, and in these circumstances only, the initial concentration [H] of analyte in the fluid is related to the fraction $(Ab/Ab_o)$ of binding sites on the binding agent occupied by the analyte by the equation:

$$Ab/Ab_o = K_{ab}[H]/1 + K_{ab}[H]$$

where $K_{ab}$ (hereinafter referred to as K) is the equilibrium constant for the binding of the analyte to the binding sites and is a constant for a given analyte and binding agent at any one temperature. This constant is generally known as the affinity constant, especially when the binding agent is an antibody, for example a monoclonal antibody.

The concept of using only a trace amount of binding agent is contrary to generally recommended practice in the field of immunoassay and immunometric techniques. For example, in such a well-known work as "Methods in Investigative and Diagnostic Endocrinology", ed. S. A. Berson and R. S. Yalow, 1973 at pages 111-116, it is proposed that in the performance of a competitive immunoassay maximum sensitivity of the assay is achieved if the proportion of the "tracer" analyte that is bound approximates to 50%. In order to achieve such a high degree of binding of the analyte the theory of Berson and Yalow, to this day generally accepted by other workers in the field, requires that the concentration of binding agent (or, strictly speaking, of binding sites, each molecule of binding agent conventionally having one or at most two binding sites) must be greater than or equal to the reciprocal of the equilibrium constant (K) of the binding agent for the analyte, i.e. [ab]>1/K. For a sample of volume V the total amount of binding agent (or binding sites) must therefore be greater than or equal to V/K. A binding agent which is a monoclonal antibody may, for example, have an equilibrium constant (K) which is of the order of $10^{11}$ liters/mole for the specific antigen to which it binds. Thus, under the above generally accepted practice, a binding agent (or site) concentration of the order of $10^{-11}$ mole/liter or more is required for binding agents of such an equilibrium constant and, with fluid sample volumes of the order of 1 milliliter, the use of $10^{-14}$ or more mole of binding agent (or site) is conventionally deemed necessary. Avogadro's number is about $6 \times 10^{23}$ so that $10^{-14}$ mole of binding site is equivalent to more than $10^9$ molecules of binding agent even assuming that the binding agent possesses two binding sites per molecule. For specific binding agents of the very highest affinity K is less than $10^{13}$ liters/mole so that conventional practice requires more than $10^7$ molecules of binding agent, whereas binding agents with lower affinity of the order of $10^8$ liters/mole necessitate the use of more than $10^{12}$ molecules under conventional practice. In fact all immunoassay kits marketed commercially at the present time conform to these concepts and use an amount of binding site approximating to or, more frequently, considerably in excess of V/K; indeed in certain types of kit relying on the use of labelled antibodies it is conventional to use as much binding agent as possible, binding proportions of analyte greatly exceeding 50%.

Because of the binding of substantial proportions, for example 50%, of the analyte in the liquid samples under test in such systems, the fractional occupancy of the binding sites of the binding agent is not independent of the volume of the fluid sample so that for accurate quantitative assays it is necessary to control accurately the volume of the sample, keeping it constant in all tests, whether of the sample of unknown concentration or of the standard samples of known concentration used to generate the dose response curve. Furthermore, such systems also require careful control of the amount of binding agent present in the standard and control incubation tubes. These limitations of present techniques are universally recognised and accepted.

UK Patent Application 2,099,578A discloses a device for immunoassays comprising a porous solid support to which antigens, or less frequently immunoglobulins, are bound at a plurality of spaced apart locations, said device permitting a large number of qualitative or quantitative immunoassays to be performed on the same support, for example to establish an antibody profile of a sample of human blood serum. However, although the individual locations may be in the form of so-called microdots produced by supplying droplets of antigen-containing solutions or suspensions, the number of moles of antigen present at each location is apparently still envisaged as being enough to bind essentially all of the analyte (e.g. antibody) whose concentration is to be measured that is present in the liquid sample under test. This is apparent from the fact that the quantitative method used in that application (page 3, lines 21-28) involves calibration with known amounts of immunoglobulin being applied to the support; but this means that, in the samples being tested, essentially every molecule must be extracted from the sample in order for a true comparison to be made and hence that large amounts of antigen (i.e. the binding agent in this situation) are required in each microdot, greatly in excess of the total amount of analyte (i.e. antibody in this situation) present in the sample.

SUMMARY OF THE INVENTION

The present invention involves the realisation that the use of high quantities of binding agent is neither necessary for good sensitivity in immunoassays nor is it generally desirable. If, instead of being kept as large as possible, the amount of binding agent is reduced so that only an insignificant proportion of the analyte is reversibly bound to it, generally less than 10%, usually less than 5% and for optimum results only 1 or 2% or less, not only is it no longer necessary to use an accurately controlled, constant volume for all the liquid samples (standard solutions and unknown samples) in a given assay, but it is also possible to obtain reliable and sometimes even improved estimates of analyte concentration using much less than V/K moles of binding agent binding sites, say not more than 0.1 V/K and preferably less than 0.01 V/K. For a binding agent having an equilibrium constant (K) for the analyte of the order of $10^{11}$ liters/mole and samples of approximately 1 ml size this is approximately equivalent to not more than $10^8$, preferably less than $10^7$, molecules of binding agent at each location in an individual array. If the value of K is $10^{13}$ liters/mole the figures are $10^6$ and $10^5$ molecules respectively, and if K is of the order of $10^8$ liters/mole they are $10^{11}$ and $10^{10}$ molecules respectively. Below $10^2$ molecules of binding agent at a single location the accuracy of the measurement would become progressively less as the fractional occupancy of the binding agent sites by the analyte would be able to change only in discrete steps as individual sites become occupied or unoccupied, but in principle at least the use of as low as 10 molecules would be permissible if an estimate with an accuracy of 10% is acceptable. Practical considerations may give rise to a preference for more than $10^4$ molecules.

It will be appreciated that the abovementioned GB patent application 2,099,578A, which for quantitative estimation relies on large amounts of binding agent and essentially total sequestration of all analyte, fails to recognise the advance achieved by the present invention, which instead relies on a different analytical principle requiring measurement of the fractional occupancy of the binding agent and which thus requires only a very low proportion of the total analyte molecules present to be sequestered from the sample.

Following the recognition that the use of such small amounts of binding agent is permissible, it becomes feasible to place the binding agent required for a single concentration measurement on a very small area of a solid support and hence to place in juxtaposition to one another but at spatially separate points on a single solid support a wide variety of different binding agents specific for different analytes which are or may be present simultaneously in a liquid to be analysed. Simultaneous exposure of each of the separate points to the liquid to be analysed will cause each binding agent spot to take up the analyte for which it is specific to an extent (i.e. fractional binding site occupancy) representative of the analyte concentration in the liquid, provided only that the volume of solution and the analyte concentration therein are large enough that only an insignificant fraction (generally less than 10%, usually less than 5%) of the analyte is bound to the point. The fractional binding site occupancy for each binding agent can then be determined using separate site-recognition reagents which recognise either the unfilled binding sites or filled binding sites of the different binding agents and which are labelled with markers enabling the concentration levels of the separate reagents bound to the different binding agents to be measured, for example fluorescent markers. Such measurements may be performed consecutively, for example using a laser which scans across the support, or simultaneously, for example using a photographic plate, depending on the nature of the labels. Other imaging devices such as a television camera can also be used where appropriate. Because the binding agents are spatially separate from one another it is possible to use only a small number of different marker labels or even the same marker label throughout and to scan each binding agent location separately to determine the presence and concentration of the label. By use of the invention considerably more than 3 analyses can be performed with a single exposure of the solid support with liquid to be analysed, for example 10, 20, 30, 50 or even up to 100 or several hundreds of analyses.

Overall, therefore, the present invention provides a method for determining the ambient concentrations of a plurality of analytes in a liquid sample of volume V liters, comprising:

loading a plurality of different binding agents, each being capable of reversibly binding an analyte which is or may be present in the liquid and is specific for that analyte as compared to the other components of the liquid sample, onto a support means at a plurality of spaced apart locations such that each location has not more than 0.1 V/K moles of a single binding agent, where K liters/mole is the equilibrium constant of the binding agent for the analyte, contacting the loaded support means with the liquid sample to be analysed such that each of the spaced apart locations is contacted in the same operation with the liquid sample, the amount of liquid used in the sample being such that only an insignificant proportion of any analyte present in the liquid sample becomes bound to the binding agent specific for it, and measuring a parameter representative of the fractional occupancy by the analytes of the binding agents at the spaced apart locations by a competitive or non-competitive assay technique using a site-recognition reagent for each binding agent capable of recognising either the unfilled binding sites or the filled binding sites on the binding agent, said site-recognition reagent being labelled with a marker enabling the amount of said reagent in the particular location to be measured.

The invention also provides a device for use in determining the ambient concentrations of a plurality of analytes in a liquid sample of volume V liters, comprising a solid support means having located thereon at a plurality of spaced apart locations a plurality of different binding agents, each binding agent being capable of reversibly binding an analyte which is or may be present in the liquid sample and is specific for that analyte as compared to the other components of the liquid sample, each location having not more than 0.1 V/K, preferably less than 0.01 V/K, moles of a single binding agent, where K liters/mole is the equilibrium constant of that binding agent for reaction with the analyte to which it is specific.

A kit for use in the method according to the invention comprises a device according to the invention, a plurality of standard samples containing known concentrations of the analytes whose concentrations in the liquid sample are to be measured and a set of labelled site-recognition reagents for reaction with filled or unfilled binding sites on the binding agents.

In arriving at the method of the invention, I have found that, generally speaking, for antibodies having an affinity constant K liters/mole for an antigen, the relationship between the antibody concentration and the fractional occupancy of the binding sites at any particular antigen concentration and the relationship between the antibody concentration and the percentage of antigen bound to the binding sites at any particular antigen concentration follow the same curves provided that the antibody concentrations and the antigen concentrations are each expressed in terms of fractions or multiples of $1/K$.

BRIEF DESCRIPTION OF THE DRAWINGS

The principle underlying the method of the invention may be better understood by reference to the accompanying drawing which is a graph representing two sets of curves plotting the relationship between antibody concentration and the fractional occupancy of the binding sites at certain prescribed antigen concentrations and the relationship between antibody concentration and the percentage of antigen bound to the binding sites at the same prescribed antigen concentrations. Each curve relates to the antibody concentration [Ab], expressed in terms of $1/K$, plotted along the x-axis. For the set of curves which remain constant or decline with increasing [Ab], the y-axis represents the fractional occupancy (F) of binding sites on the antibody by the antigen; for the second set, the y-axis represents the percentage (b%) of antigen bound to those Binding sites. The individual curves in each set represent the relationships corresponding to four different antigen concentrations [Ann] expressed in terms of K, namely $10/K$, $1.0/K$, $0.1/K$ and $0.01/K$. The curve show that as [Ab] falls F reaches an essentially constant level, the value of which is dependent on [An].

DETAILED DESCRIPTION

The choice of a solid support is a matter to be left to the user. Preferably the support is non-porous so that the binding agent is disposed on its surface, for example as a monolayer. Use of a porous support may cause the binding agent, depending on its molecular size, to be carried down into the pores of the support where its exposure to the analyte whose concentration is to be determined may likewise be affected by the geometry of the pores, so that a false reading may be obtained. Porous supports such as nitrocellulose paper dotted with spots of binding agent are therefore less preferred, Unlike the supports used in GB 2,099,578A, which seem to need to be porous because of the large number of molecules to be attached, the supports for use in the present invention use much smaller quantities and therefore need not be porous. The non-porous supports may, for example be of plastics material or glass, and any convenient rigid plastics material may be used, Polystyrene is a preferred plastics material, although other polyolefins or acrylic or vinyl polymers could likewise be used.

The support means may comprise microbeads, e.g. of such a plastics material, which can be coated with uniform layers of binding agent and retained in specified locations, e.g. hollows, on a support plate, Alternatively the material may be in the form of a sheet or plate which is spotted with an array of dots of binding agent, It can be advantageous for the configuration of the support means to be such that liquid samples of approximately the volume V liters are readily retained in contact with the plurality of spaced apart locations marked with the different binding agents, For example, the spaced apart locations may be arranged in a well in the support means, and a plurality of wells, each provided with the same group of different binding agents in spaced apart locations, can be linked together to form a microliter plate for use with a plurality of samples.

When the support means is to be used in conjunction with a measuring system involving light scanning, the material, e.g. plastics, for the support is desirably opaque to light, for example it may be filled with an opacifying material which may inter alia be white or black, such as carbon black, when the signals to be measured from the binding agent or the site-recognition reagent are light signals, as from fluorescent or luminescent markers. In general, reflective materials are preferred in this case to enhance light collection in the detecting instrument or photographic plate. The final choice of optimum material is governed by its ability to attach the binding agent to its surface, its absence of background signal emission and its possession of other properties tending to maximise the signal/noise ratio for the particular marker or markers attached to the binding agent situated on its surface. Very satisfactory results have been obtained in the Examples described below by the use of a white opaque polystyrene microliter plate commercially available from Dynatech under the trade name White Microfluor microliter wells.

The binding agents used may be binding agents of different specificity, that is to say agents which are specific to different analytes, or two or more of them may be binding agents of the same specificity but of different affinity, that is to say agents which are specific to the same analyte but have different equilibrium constants K for reaction with it. The latter alternative is particularly useful where the concentration of analyte to be assayed in the unknown sample can vary over considerable ranges, for example 2 or 3 orders of magnitude, as in the case of HCG measurement in urine of pregnant women, where it can vary from 0.1 to 100 or more IU/ml.

The binding agents used will preferably be antibodies, more preferably monoclonal antibodies. Monoclonal antibodies to a wide variety of ingredients of biological fluids are commercially available or may be made by known techniques. The antibodies used may display conventional affinity constants, for example from $10^8$ or $10^9$ liters/mole upwards, e.g. of the order of $10^{10}$ or $10^{11}$ liters/mole, but high affinity antibodies with affinity constants of $10^{12}$–$10^{13}$ liters/mole can also be used. The invention can be used with such binding agents which are not themselves labelled. However, it is also possible and frequently desirable to use labelled binding agents so that the system binding agent/analyte/site-recognition reagent includes two different labels of the same type, e.g. fluorescent, chemiluminescent, enzyme or radioisotopic, one on the binding agent and one on the site-recognition reagent. The measuring operation then measures the ratio of the intensity of the two signals and thus eliminates the need to place the same amount of labelled binding agent on the support when measuring signals from standard samples for calibration purposes as when measuring signals from the unknown samples. Because the system depends solely on measurement of a ratio representative of binding site occupancy, there is also no need to measure the signal from the entire spot but scanning only a portion is sufficient. Each binding agent is preferably labelled with the same label but different labels can be used.

The binding agents may be applied to the support in any of the ways known or conventionally used for coating binding agents onto supports such as tubes, for example by contacting each spaced apart location on the support with a solution of the binding agent in the form of a small drop, e.g. 0.5 microliter, on a 1 mm² spot, and allowing them to remain in contact for a period of time before washing the drops away. A roughly constant small fraction of the binding agent present in the drop becomes adsorbed onto the support as a result of this procedure. It is to be noted that the coating density of binding agent on the microspot does not need to be less than the coating density in conventional antibody-coated tubes; the reduction in the number of molecules on each spot may be achieved solely by reduction of the size of the spot rather than the coating density. A high coating density is generally desirable to maximise signal/noise ratios. The sizes of the spots are advantageously less than 10 mm² preferably less than 1 mm². The separation is desirably, but not necessarily, 2 or 3 times the radius of the spot, or more. These suggested geometries can nevertheless be changed as required, being subject solely to the limitations on the number of binding agent molecules in each spot, the minimum volume of the sample to which the array of spots will be exposed and the means locally available for conveniently preparing an array of spots in the manner described.

Once the binding agents have been coated onto the support it is conventional practice to wash the support, in the case of antibodies as binding agents, with a solution containing albumen or other protein to saturate all remaining non-specific adsorption sites on the support and elsewhere. To confirm that the amount of binding agent in an individual spot will be less than the maximum amount (0.1 V/K) required to conform to the principle of the present invention, the amount of binding agent present on any individual site can be checked by labelling the binding agent with a detectable marker of known specific activity (i.e. known amount of marker per unit weight of binding agent) and measuring the amount of marker present. Thus, if the use of labelled binder is not desired on the solid support used in the method of the invention the binding agent can nevertheless be labelled in a trial experiment and identical conditions to those found in that trial to give rise to correct loadings of binding agent can be used to apply unlabelled binding agent to the supports to be actually used.

The minimum size of the liquid sample (V liters) is correlated with the number of mole of binding agent (less than 0.1 V/K) so that only an insignificant proportion of the analyte present in the liquid sample becomes bound to the binding agent. This proportion is as a general rule less than 10%, usually less than 5% and desirably 1 or 2% or less, depending on the accuracy desired for the assay (greater accuracy being obtained, other things being equal, when smaller pro portions of analyte are bound) and the magnitude of other error-introducing factors present. Sample sizes of the order of one or a few ml or less, e.g. down to 100 microliters or less, are often preferred, but circumstances may arise when larger volumes are more conveniently assayed, and the geometry may be adjusted accordingly. The sample may be used at its natural concentration level or if desired it may be diluted to a known extent.

The site-recognition reagents used in the method according to the invention may themselves be antibodies, e.g. monoclonal antibodies, and may be anti-idiotypic or anti-analyte antibodies, the latter recognising occupied sites. Alternatively, for example for analytes of small molecular size such as thyroxine (T4), unoccupied sites may be recognised using either the analyte itself, appropriately labelled, or the analyte covalently coupled to another molecule—e.g. a protein molecule—which is directly or indirectly labelled. The site-recognition reagents may be labelled directly or indirectly with conventional fluorescent labels such as fluorescein, rhodamine or Texas Red or materials usable in time-resolved pulsed fluorescence such as europium and other lanthanide chelates, in a conventional manner. Other labels such as chemiluminescent, enzyme or radioisotopic labels may be used if appropriate. Each site-recognition reagent is preferably labelled with the same label but different labels can be used in different reagents. The site-recognition reagents may be specific for a single one of the binding agent/analyte spots in each group of spots or in certain circumstances, as with glycoprotein hormones such as HCG and FSH which have a common binding site, they may be cross-reacting reagents able to react with occupied binding sites in more than one of the spots.

In the assay technique the signals representative of the fractional occupancy of the binding agent in the test samples of unknown concentrations of the analytes can be calibrated by reference to dose response curves obtained from standard samples containing known concentrations of the same analytes. Such standard samples need not contain all the analytes together, provided that each of the analytes is present in some of the standard samples. Fractional occupancy may be measured by estimating occupied binding sites (as with an anti-analyte antibody) or unoccupied binding sites (as with an anti-idiotypic antibody), as one is the converse of the other. For greater accuracy it is desirable to measure the fraction which is closer to zero because a change in fractional occupancy of 0.01 is proportionately greater in this case, although for fractional occupancies in the range 25–75% either alternative is generally satisfactory.

In that embodiment of the present invention which relies on two fluorescent markers, the measurement of relative intensity of the signals from the two markers, one on the binding agent and the other on the site recognition reagent, may be carried out by a laser scanning confocal microscope such as a Bio-Rad Lasersharp MRC 500, available from Bio-Rad Laboratories Ltd., and having a dual channel detection system. This instrument relies on a laser beam to scan the dots or the like on the support to cause fluorescence of the markers and wavelength filters to distinguish and measure the amounts of fluorescence emitted. Time-resolved fluorescence methods may also be used. Interference (so-called crosstalk) between the two channels can be compensated for by standard corrections if it occurs or conventional efforts can be made to reduce it. Discrimination of the two fluorescent signals emitted by the dual-labelled spots is accomplished in the present form of this instrument, by filters capable of distinguishing the characteristic wavelength of the two fluorescent emissions; however, fluorescent substances may be distinguished by other physical characteristics such as differing fluorescence decay times, bleaching times, etc., and any of these means may be used, either alone or in combination, to differentiate between two fluorophores and hence permit measurement of the ratio of two fluorescent labelled entities (binding agent and site-recognition reagent) present on an individual spot, using techniques well known in the fluorescence measurement field. When only one fluorescent label is present the same techniques may be used, provided that care is taken to scan the entire spot in each case and the spots contain essentially the same amount of binding agent from one assay to the next when the unknown and standard samples are used.

In the case of other labels, such as radioisotopic labels, chemiluminescent labels or enzyme labels, analogous means of distinguishing the individual signals from one or from each of a pair of such labels are also well known, For example two radioisotopes such as $^{125}I$ and $^{131}I$ may be readily distinguished on the basis of the differing energies of their respective radioactive emissions. Likewise it is possible to identify the products of two enzyme reactions, deriving from dual enzyme-labelled antibody couplets, these being e.g. of different colours, or two chemiluminescent reactions, e.g. of different chemiluminescent lifetime or wavelength of light emission, by techniques well known in the respective fields.

The invention may be used for the assaying of analytes present in biological fluids, for example human body fluids such as blood, serum, saliva or Urine. They may be used for the assaying of a wide variety of hormones, proteins, enzymes or other analytes which are either present naturally in the liquid sample or may be present artificially such as drugs, poisons or the like.

For example, the invention may be used to provide a device for quantitatively assaying a variety of hormones relating to pregnancy and reproduction, such as FSH, LH, HCG, prolactin and steroid hormones (e.g. progesterone, estradiol, testosterone and androstene-dione), or hormones of the adrenal pituitary axis, such as cortisol, ACTH and aldosterone, or thyroid-related hormones, such as T4, T3, and TSH and their binding protein TBG, or viruses such as hepatitis, AIDS or herpes virus, or bacteria, such as staphylococci, streptococci, pneumococci, gonococci and enterococci, or tumour-related peptides such as AFP or CEA, or drugs such as those banned as illicit improvers of athletes' performance, or food contaminants. In each case the binding agents used will be specific for the analytes to be assayed (as compared with others in the sample) and may be monoclonal antibodies therefor.

Further details on the methodology are to be found in my International Patent Publication W088/01058, the contents of which are incorporated herein by reference.

The invention is illustrated by the following Examples.

EXAMPLE 1

An anti-TNF (tumour necrosis factor) antibody having an affinity constant for TNF at 25° C. of about $1 \times 10^9$ liters/mole is labelled with Texas Red. A solution of the antibody at a concentration of 80 micrograms/ml is formed and 0.5 microliter aliquots of this solution are added in the form of droplets one to each well of a Dynatech Microfluor (opaque white) filled polystyrene microliter plate having 12 wells.

An anti-HCG (human chorionic gonadotropin) antibody having an affinity constant for HCG at 25° C. of about $6 \times 10^8$ liters/mole is also labelled with Texas Red. A solution of the antibody at a concentration of 80 micrograms/ml is formed and 0.5 microliter aliquots of this solution are added in the form of droplets one to each well of the same Dynatech Microfluor microliter plate.

After addition of the droplets the plate is left for a few hours in a humid atmosphere to prevent evaporation of the droplets. During this time some of the antibody molecules in the droplets become adsorbed onto the plate. Next, the wells are washed several times with a phosphate buffer and then they are filled with about 400 microliters of a 1% albumen solution and left for several hours to saturate the residual binding sites in the wells. Thereafter they are washed again with phosphate buffer.

The resulting plate has in each of its wells two spots each of area approximately 1 mm$^2$. Measurement of the amount of fluorescence shows that in each well one spot contains about $5 \times 10^9$ molecules of anti-TNF antibody and the other contains about $5 \times 10^9$ molecules of anti-HCG antibody. The wells are designed for use with liquid samples of volume 400 microliters, so that 0.1 V/K is $4 \times 10^{-14}$ moles (equivalent to $2.4 \times 10^{10}$ molecules) for the anti-TNF antibody and $7 \times 10^{-14}$ moles (equivalent to $4 \times 10^{10}$ molecules) for the anti-HCG antibody.

EXAMPLE 2

A microliter plate prepared as described in Example 1 is used in an assay for an artificially produced solution containing TNF and HCG. A test sample of the solution, amounting to about 400 microliters, is added to one of the wells and allowed to incubate for several hours. About 400 microliters of various standard solutions containing known concentrations (0.02, 0.2, 2 and 20 ng/ml) of TNF or HCG are added to other wells of the plate and also allowed to incubate for several hours. The wells are then washed several times with buffer solution.

As site-recognition reagents there are used for the TNF spots an anti-TNF antibody having an affinity constant for TNF at 25° C. of about $1 \times 10^{10}$ liters/mole and for the HCG spots an anti-HCG antibody having an affinity constant for HCG at 25° C. of about $1 \times 10^{11}$ liters/mole. Both antibodies are labelled with fluorescein (FITC). 400 microliter aliquots of solutions of these labelled antibodies are added to the wells and allowed to stand for a few hours. The wells are then washed with buffer.

The resulting fluorescence ratio of each spot is quantified with a Bio-Rad Lasersharp MRC 500 confocal microscope. From the standard solutions dose response curves for TNF and HCG are built up, the figures for TNF being as follows:

| TNF concentration ng/ml | $\frac{\text{FITC fluorescence}}{\text{Texas Red fluorescence}}$ on TNF spot |
|---|---|
| 0.02 | 1.1 |
| 0.2 | 4.6 |
| 2 | 7.9 |
| 20 | 42.5 | and those for HCG being as follows:

| HCG concentration ng/ml | $\frac{\text{FITC fluorescence}}{\text{Texas Red fluorescence}}$ on HCG spot |
|---|---|
| 0.02 | 1.8 |
| 0.2 | 7.2 |

| HCG concentration ng/ml | $\dfrac{\text{FITC fluorescence}}{\text{Texas Red fluorescence}}$ on HCG spot |
| --- | --- |
| 2 | 16.0 |
| 20 | 28.2 |

The artificially produced solution was found to give ratio readings of 5.9 on the TNF spot and 10.5 on the HCG spot, correlating well with the actual concentrations of TNF (0.5 ng/ml) and HCG (0.5 ng/ml) obtained from the dose response curves.

EXAMPLE 3

Using similar procedures to those outlined in Example 1 a microliter plate containing spots of labelled anti-T4 (thyroxine) antibody (affinity constant about $1 \times 10^{11}$ liters/mole at 25° C), labelled anti-TSH (thyroid stimulating hormone) antibody (affinity constant about $5 \times 10^9$ liters/mole at 25° C.) and labelled anti-T3 (triiodothyronine) antibody (affinity constant about $1 \times 10^{11}$ liters/mole at 25° C.) in each of the individual wells is produced, the spots containing less than $1 \times 10^{-12}$ V moles of anti-T4 antibody or less than $2 \times 10^{-11}$ V moles of anti-TSH antibody or less than $1 \times 10^{-12}$ V moles of anti-T3 antibody.

The developing antibody (site-recognition reagent) for the TSH assay is an anti-TSH antibody with an affinity constant for TSH of $2 \times 10^{10}$ liters/mole at 25° C. This antibody is labelled with fluorescein (FITC). The site-recognition reagents for the T4 and T3 assays are T4 and T3 coupled to poly-lysine and labelled with FITC, and they recognise the unfilled sites on their respective first antibodies.

Using 400 microliter aliquots of standard solutions containing various known amounts of T4, T3 and TSH, dose response curves are obtained by methods analogous to those in Example 2, correlating fluorescence ratios with T4, T3 and TSH concentrations. The plate is used to measure T4, T3 and TSH levels in serum from human patients with good correlation with the results obtained by other methods.

EXAMPLE 4

Using similar procedures to those outlined in Example 1 a microliter plate containing spots of first labelled anti-HCG antibody (affinity constant about $6 \times 10^8$ liters/mole at 25° C.), second labelled anti-HCG antibody (affinity constant about $1.3 \times 10^{11}$ liters/mole at 25° C.) and labelled anti-FSH (follicle stimulating hormone) antibody (affinity constant about $1.3 \times 10^8$ liters/mole at 25° C.) in each of the individual wells is produced, the spots each containing less than 0.1 V/K moles of the respective antibody. A cross-reacting (alpha subunit) monoclonal antibody 8D10 with an affinity constant of $1 \times 10^{11}$ liters/mole is used as a common developing antibody for both the HCG and the FSH assays.

Using 400 microliter aliquots of standard solutions containing various known concentrations of HCG and FSH, dose response curves are obtained by methods analogous to those in Example 2, correlating fluorescence ratios with HCG and FSH concentrations, the curve obtained with the higher affinity anti-HCG antibody giving more concentration-sensitive results at the lower HCG concentrations whereas the curve from the lower affinity anti-HCG antibody is more concentration-sensitive at the higher HCG concentrations. The plate is used to measure HCG and FSH concentrations in the urine of women in pregnancy testing, giving good correlations with results obtained by other means and achieving effective concentration measurements for HCG over a concentration range of two or three orders of magnitude by correct choice of the best HCG spot and dose response curve.

Production of labelled antibodies

The labelling of the antibodies with fluorescent labels can be carried out by a well known and standard technique, see Leslie Hudson and Frank C. Hay, "Practical Immunology", Blackwell Scientific Publications (1980), pages 11–13, for example as follows:

The monoclonal antibody anti-FSH 3G3, an FSH specific (beta subunit) antibody having an affinity constant (K) of $1.3 \times 10^8$ liters per mole, was produced in the Middlesex Hospital Medical School, and was labelled with TRITC (rhodamine isothiocyanate) or Texas Red, giving a red fluorescence.

The monoclonal antibody anti-FSH 8D10, a cross-reacting (alpha subunit) antibody having an affinity constant (K) of $1 \times 10^{11}$ liters per mole, was likewise produced in the Middlesex Hospital Medical School and was labelled with FITC (fluorescein isothiocyanate), giving a yellow-green fluorescence.

The general procedure used involved ascites fluid purification (ammonium sulphate precipitation and T-gel chromatography) followed by labelling, according to the following steps:

1.a. Ammonium sulphate purification

1. Add 4.1 ml saturated ammonium sulphate solution to 5 ml anti body preparation (culture supernatant or 1:5 diluted ascites fluid) under constant stirring (45% saturation).

2. Continue stirring for 30–90 min. Centrifuge at 2500 rpm for 30 min.

3. Discard the supernatant and dissolve the precipitate in PBS (final volume 5 ml.). Repeat Steps 1 and 2, OR.

4. Add 3.6 ml saturated ammonium sulphate (40% saturation) under constant stirring. Repeat Step 2.

5. Discard the supernatant and dissolve the pellet in the desired buffer.

6. Dialyse overnight in cold against the same buffer (using fresh, boiled-in-d/w dialysis bag).

7. Determine the protein concentration either at $A_{280}$ or by Lowry estimation.

1.b. T-gel Chromatography: (Buffer: 1M Tris-Cl, pH 7.6. Solid potassium sulphate)

1. Clear 2 ml of ascites fluid by centrifugation at 4000 rpm.

2. Add 1M Tris-Cl solution to achieve final concentration of 0.1M.

3. Add sufficient amount of solid potassium sulphate. Final concentration:=0.5M.

4. Apply the ascite fluid to the T-gel column.

5. Wash the column with 0.1M Tris-Cl buffer containing 0.5M potassium sulphate, until protein profile (at $A_{280}$) returns to zero.

6. Elute the absorbed protein using 0.1M Tris-Cl buffer as the eluant.

7. Pool the fractions containing antibody activity and concentrate using Amicon 30 concentrater.

8. If HPHT purification is to be carried out, use HPHT chromatography Starting buffer during Step 7.

2. Labelling of Antibodies FITC/TRITC conjugation:

1. Dialyse the purified 1 g protein into 0.25M Carbonate-bicarbonate buffer, pH 9.0 to a concentration of 20 mg/ml.
2. Add FITC/TRITC to achieve a 1:20 ratio with protein (i.e. 0.05 mg for every 1 mg of protein).
3. Mix and incubate at 4° C. for 16–18 hrs.
4. Separate the conjugated protein from unconjugated by:
   a. Sephadex G-25 chromatography for FITC label, or
   b. DEAE-Sephacel chromatography for TRITC-/FITC label.
   Buffer system:
   PBS for (a).
   0.005M Phosphate, pH 8.0 and 0.18M Phosphate, pH 8.0 for (b).

$$\frac{2.87 \times O.D.495 \text{ nm}}{O.D.280 \text{ nm} - 0.35 \times O.D.495 \text{ nm}}$$

I claim:

1. A method for determining the ambient concentrations of a plurality of analytes in a liquid sample of volume V liters, comprising:
   loading a plurality of different binding agents, each being capable of reversibly binding an analyte which is or may be present in the liquid sample and is specific for said analyte as compared to the other components of the liquid sample, onto a support means at a plurality of spaced apart small spots such that each spot has a high coating density of one of said binding agents but not more than 0.1 V/K moles of binding agent are present on any spot, where K liters/mole is the affinity constant of said binding agent for said analyte;
   contacting the loaded support means with the liquid sample to be analyzed, such that each of the spots is contacted in the same step with said liquid sample, the amount of liquid used in said sample being such that only an insignificant proportion of any analyte present in said liquid sample becomes bound to said binding agent specific for said analyte, and
   measuring a parameter representative of the fractional occupancy by said analytes of said binding agents at the spots by a competitive or non-competitive assay technique using a site-recognition reagent for each binding agent capable of recognizing either the unfilled binding sites or the filled binding sites on said binding agent, said site-recognition reagent being labelled with a marker enabling the amount of said reagent in the particular location to be measured.

2. A method as claimed in claim 1, wherein each of said spots has a size of less than 1 mm$^2$.

3. A method as claimed in claim 2, wherein each of said spots contains more than 10$^4$ molecules of binding agent.

4. A method as claimed in claim 3, wherein each of said spots has less than 0.01 V/K moles of binding agent.

5. A method as claimed in claim 3, wherein said binding agents used have affinity constants for said analytes of from 10$^8$ to 10$^{13}$ liters per mole.

6. A method as claimed in claim 3, wherein said binding agents used have affinity constants for said analytes of the order of 10$^{10}$ or 10$^{11}$ liters per mole.

7. A method as claimed in claim 3, wherein the volume of said liquid sample is not more than 0.1 liter.

8. A method as claimed in claim 3, wherein the volume of said liquid sample is 400 to 1000 microliters.

9. A method as claimed in claim 1, wherein said binding agents loaded onto said support means are antibodies for the analytes whose concentrations are to be determined.

10. A method as claimed in claim 1, wherein said binding agents are labelled with markers enabling the concentration levels of said binding agents to be measured.

11. A method as claimed in claim 10, wherein said binding agents and said site-recognition reagents are labelled with fluorescent markers such that at the individual spots the assay technique for measuring fractional occupancy of the binding agents measures the ratios of the signals emitted by the fluorescent markers.

12. A device for use in determining the ambient concentrations of a plurality of analytes in a liquid sample of volume V liters, comprising a solid support means having located thereon at high coating density at a plurality of spaced apart small spots a plurality of different binding agents, each binding agent being capable of reversibly binding an analyte which is or may be present in said liquid sample and is specific for said analyte as compared to the other components of said liquid sample, each spot having not more than 0.1 V/K moles of a single binding agent, where K liters/mole is the affinity constant of said single binding agent for reaction with the analyte to which it is specific.

13. A device as claimed in claim 12, wherein each of said spots has a size of less than 1 m$^2$.

14. A device as claimed in claim 13, wherein each of said spots contains more than 10$^4$ molecules of binding agent.

15. A kit for use in determining the ambient concentration of a plurality of analytes in a liquid sample of volume V liters, comprising:
   a solid support means having located thereon at high coating density at a plurality of spaced apart small spots a plurality of different binding agents, each binding agent being capable of reversibly binding an analyte which is or may be present in said liquid sample and is specific for said analyte as compared to the other components of the liquid sample, each spot having not more than 0.1 V/K moles of a single binding agent, where K liters/mole is the affinity constant of said single binding agent for reaction with the analyte to which it is specific;
   a plurality of standard samples containing known concentrations of the analytes whose concentrations in the liquid sample are to be measured; and
   a set of labelled site-recognition reagents for reaction with filled or unfilled binding sites on said binding agents.

16. A kit as claimed in claim 15, wherein each of said spots has a size of less than 1 mm$^2$.

17. A kit as claimed in claim 16, wherein each of said spots contains more than 10$^4$ molecules of binding agent.

* * * * *

UNITED STATES PATENT AND TRADEMARK OFFICE
CERTIFICATE OF CORRECTION

PATENT NO. : 5,432,099

DATED : July 11, 1995

INVENTOR(S) : Roger P. EKINS

It is certified that error appears in the above-identified patent and that said Letters Patent is hereby corrected as shown below:

On the title page: Item [30]

"Foreign Application Priority Data", after "Feb. 10, 1988 [GB] United Kingdom ......... 8803000" insert
--Aug.6,1987 [WO]  ........ PCT/GB87/00558 --.

Signed and Sealed this

Tenth Day of November 1998

Attest:

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO.   : 5,432,099
DATED        : July 11, 1995
INVENTOR(S)  : Roger P. Ekins It is certified that error appears in the above-identified patent and that said Letters Patent is hereby corrected as shown below:

Column 14,
Line 36, "$m^2$" should read -- $mm^2$ --.

Signed and Sealed this

Twenty-third Day of December, 2003

JAMES E. ROGAN
*Director of the United States Patent and Trademark Office*

(12) EX PARTE REEXAMINATION CERTIFICATE (5658th)
United States Patent
Ekins

(10) Number: US 5,432,099 C1
(45) Certificate Issued: Jan. 23, 2007

(54) DETERMINATION OF AMBIENT CONCENTRATION OF SEVERAL ANALYTES

(75) Inventor: Roger P. Ekins, London (GB)

(73) Assignee: Multilyte Limited, Bradford-on-Avon (GB)

Reexamination Request:
No. 90/006,852, Nov. 10, 2003
No. 90/006,972, Mar. 22, 2004
No. 90/007,266, Oct. 25, 2004

Reexamination Certificate for:
Patent No.: 5,432,099
Issued: Jul. 11, 1995
Appl. No.: 07/984,264
Filed: Dec. 1, 1992

Certificate of Correction issued Nov. 10, 1998.

Certificate of Correction issued Dec. 23, 2003.

Related U.S. Application Data

(63) Continuation of application No. 07/460,878, filed as application No. PCT/GB88/00649 on Aug. 5, 1988, now abandoned.

(30) Foreign Application Priority Data

Aug. 6, 1987 (WO) .............................. PCT/GB87/00558
Feb. 10, 1988 (GB) ............................................. 8803000

(51) Int. Cl.
*G01N 33/543* (2006.01)

(52) U.S. Cl. ...................... 436/518; 436/501; 436/517; 435/7.1; 435/7.92; 435/973

(58) Field of Classification Search ................. 436/518, 436/517, 536; 435/7.1
See application file for complete search history.

(56) References Cited

U.S. PATENT DOCUMENTS 1,711,742 A 5/1929 Nordlander 3,001,915 A 9/1961 Fonner
3,802,842 A 4/1974 Lange et al.

(Continued)

FOREIGN PATENT DOCUMENTS

| EP | 0063810 | 11/1982 |
| EP | 0134215 | 12/1982 |
| EP | 0 015 687 A | 4/1983 |

(Continued)

OTHER PUBLICATIONS

Gallo, Dana, et al., J. Clin. Microb., vol. 13, pp. 631–636 (1981).

(Continued)

*Primary Examiner*—James Housel

(57) ABSTRACT

A method for determining the ambient concentrations of a plurality of analytes in a liquid sample of volume V liters, comprises
loading a plurality of different binding agents, each being capable of binding specifically and reversibly an analyte of interest onto a support means at a plurality of spaced apart locations such that not more than 0.1 V/K moles of each binding agent are present at any location, where k liters/mole is the equilibrium constant of each such binding agent;
contracting the loaded support means with the sample to be analyzed, such that each of the spaced apart locations is contacted in the same operation with the sample, the amount of sample liquid being such that only an insignificant proportion of any analyte present in the sample becomes bound to the binding agent specific for it, and
measuring a parameter representative of the fractional occupancy by the analytes of the binding agents at the spaced apart locations by a competitive or non-competitive assay technique, using a labelled site-recognition reagent for each binding agent capable of recognizing either the unfilled binding sites or the filled binding sites on the binding agent, which enables the amount of said reagent in the particular location to be measured. A device and kit for use in the method are also provided.

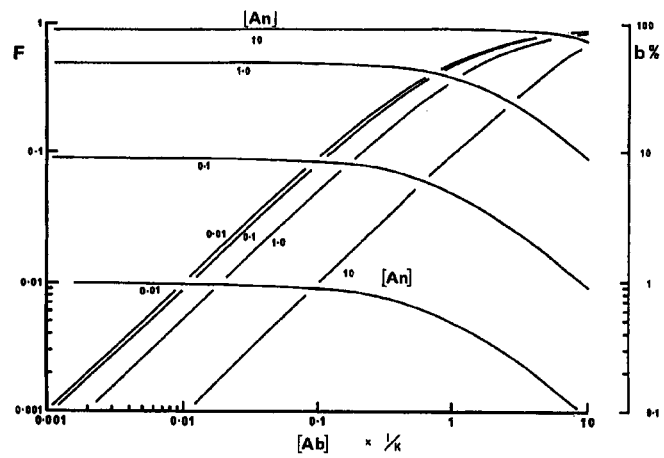

U.S. PATENT DOCUMENTS

| | | | |
|---|---|---|---|
| 3,907,503 A | 9/1975 | Betts et al. |
| 3,966,580 A | 6/1976 | Janata et al. |
| 3,992,631 A | 11/1976 | Harte |
| 4,020,830 A | 5/1977 | Johnson et al. |
| 4,054,646 A | 10/1977 | Giaever |
| 4,067,959 A | 1/1978 | Bolz |
| 4,092,116 A | 5/1978 | Giaever |
| 4,120,754 A | 10/1978 | Barendsz et al. |
| 4,236,893 A | 12/1980 | Rice |
| 4,238,757 A | 12/1980 | Schenck |
| 4,242,096 A | 12/1980 | Oliveira et al. |
| 4,299,916 A | 11/1981 | Litman et al. |
| 4,301,115 A | 11/1981 | Rapkin et al. |
| 4,385,126 A | 5/1983 | Chen et al. |
| 4,402,819 A | 9/1983 | Rechnitz et al. |
| 4,459,360 A | 7/1984 | Marinkovich |
| 4,487,839 A | 12/1984 | Kamentsky |
| 4,562,157 A | 12/1985 | Lowe et al. |
| 4,567,149 A | 1/1986 | Sell et al. |
| 4,591,570 A | 5/1986 | Chang |
| 4,647,544 A | 3/1987 | Nicoli et al. |
| 4,673,657 A | 6/1987 | Christian |
| 4,786,594 A | 11/1988 | Khanna et al. |
| 4,829,010 A | 5/1989 | Chang |
| 4,880,750 A | 11/1989 | Francoeur |
| 5,074,977 A | 12/1991 | Cheung et al. |
| 5,096,807 A | 3/1992 | Leaback |
| 5,156,953 A | 10/1992 | Litman et al. |
| 5,348,855 A | 9/1994 | Dattagupta et al. |
| 5,432,099 A | 7/1995 | Ekins |
| 5,486,452 A | 1/1996 | Gordon et al. |
| 5,599,720 A | 2/1997 | Ekins |

FOREIGN PATENT DOCUMENTS

| | | |
|---|---|---|
| EP | 0015687 B1 | 5/1984 |
| EP | 0134215 | 3/1985 |
| EP | 0190006 A1 | 8/1986 |
| EP | 0235726 | 9/1987 |
| EP | 0 304 202 | 2/1989 |
| EP | 0134215 B1 | 10/1989 |
| EP | 0304202 B1 | 7/1992 |
| GB | 2030290 | 4/1980 |
| GB | 2 099 578 A | 11/1982 |
| GB | 2099578 A | 12/1982 |
| WO | 84/01031 | 3/1984 |
| WO | 8401031 | 3/1984 |
| WO | WO 84/01031 A1 | 3/1984 |
| WO | 86/01604 | 3/1986 |
| WO | 84/03151 | 5/1986 |
| WO | 88/01058 | 2/1988 |
| WO | 90/15070 | 9/1992 |

OTHER PUBLICATIONS

Scribblers, Calligraphy Catalog, http://www.scribblers.co.uk/acatalog/speedball_C_style_nibs_righthanded.html, May 27, 2004.

Roger Ekins, Assay Design and Quality Control, In: Radioimmunology—1979 (Ch. A. Bizollon, ed.). Elsevier, North Holland Biomedical Press, Amsterdam, Netherlands, pp. 239–255.

Supplementary Declaration of E.F. Ullaman, dated Jun. 1, 2004.

Roger Ekins, Internet Forum on Microarrays and Mass Action Laws, May 14, 2000–May 16, 2000.

Page 11 of Multilyte's submission to the German tribunal presiding over the nullity action.

R. Ekins, et al. Inalytica Chimica Acta, vol. 227, pp. 73–96.

Sokolowski and Wood, Radioimmunoassay in Theory and Practice, In: A handbook for Laboratory Personnel, Schnetzior–Verlag, Konstanz, pp. 138–143 and pp. 172–173.

Sigma–Aldrich Catalog, Methyl red, 1996, p. 731.

Multilyte's opposition to plaintiff/counterdefendant Affymetrix Inc.'s motion for summary judgment of noninfringement based on the court's construction of the term "determining the ambient concentrations". Apr. 27, 2005 1:30PM, Judge Hon. William Alsup.

Multilyte Ltd.'s opposition to Affymetrix, Inc.'s motion for summary judgement of noninfringement based on the construction of the term "binding agent" Apr. 27, 2005, time 1:30PM, Judge Hon. William Alsup.

Multilyte Ltd.'s notice of motion and motion for partial summary judgement for further claim construction of the term "binding agent", Apr. 28, 2005, Judge Hon. William Alsup.

Reporter's Transcript of Proceedings *Affymetrix, Incorporated* vs. *Multilyte Limited*. Before the Honorable William Alsup, Judge, Thursday, Feb. 18, 2005. (108 pages).

Multilyte Ltds. Tutorial—Presentation Slides (85 pgs).

Order construing selected Claims terms (Feb. 22, 2005).

Order granting motion to alter or amend judgment, noting briefing schedule and vacating hearing. (May 17, 2005).

Order granting Summary Judgment of Non–Infringement. (Apr. 26, 2005).

Order granting Multilyte's motion for further claim construction and re–constructing "binding Agent".

Transcript of Proceedings, Dated Apr. 27, 2005 78 pages.

Complaint in nullity action (by Affymetrix—Oct. 15, 2003).

Reply brief (by Multilyte—Feb. 9, 2004).

Submission of Declaration of Professor Roger P. Ekins (by Multilyte—May 10, 2004).

Response to the Briefs filed on behalf of the Defendant dated Feb. 9, 2004 and May 10, 2004 (by Affymetrix—Jun. 1, 2004).

With reference to the submission of plaintiff dated Jun. 1, 2004 (by Affymetrix—Jun. 11, 2004).

On the submission of the plaintiff dated Jun. 2, 2004 and Jun. 11, 2004 (by Multilyte—Jun. 24, 2004).

Opinion of German court.

On the submissions of the plaintiff dated une 1, 2004 and Jun. 11, 2004 (by Multilyte—Jun. 23, 2004).

Sehon, In: Methods in Immunology and Immunochemistry. Ed. Williams and Chase.—NY: Academic Press, (1971). Chapter 15, p. 375–383.

Solsky and Rechnitz, Science, (1979) vol. 204, p. 1308–1309.

Nakamura and Tucker, In: Serum Protein Abnormalities. Ed. Ritzmann and Daniels, Little, Brown, & Co., Boston, (1975). Chapter 17, p. 314–330.

Casali et al., Journal of Immunology, (1989) vol. 143, p. 3476–3483.

Suenaga et al., Lupus, (1992) vol. 1, p. 363–368.

Conway De Macario et al., Journal of Immunol. Methods, (1983), vol. 59, p. 39–47.

Dissanayake et al., Immunology, (1977), vol. 32, p. 309–318.

Vonderviszt et al., Biochem. J., (1987) vol. 243, p. 449–455.

Litman et al., Clin. Chem., (1983) vol. 29, p. 1598–1603.

Ekins et al., In: Alternative Immunoassays, Ed. by. W.P. Collins, NY: Wiley (1985)., Chapter 13, p. 219–237.

Ekins et al., J. Endocrinology, 85(2):29P–30P (1980).
Giaever, Ivar: Journal of Immunology, (1976) vol. 116, No. 3, pp. 766–771.
Fodor et al., Science (1991) vol. 251, p. 767–773.
Pugia et al., J. Clin. Lab. Anal., (1999), vol. 13, p. 180–187.
D'Auria, Biomedical and Biophysical Research Communications (1999), vol. 263, p. 550–553.
Declaration of Dr. Edwin F. Ullman from Nullity action filed Oct. 15, 2003 against the German part of European Patent No. 0304202.
Ekins et al., "Multianalyte testing", Clin Chem. 39:369–370 (1992).
Dudley et al., "Guidelines for Immunoassay Data Processing", Clin. Chem. 31(1264–1271) (1985).
Declaration of Edwin F. Ullman, dated Mar. 9, 2004.
Hawkes et al., Anal. Biochem., vol. 119, p. 142–47, Fig. 5 (1982).
Modern Urine Chemistry, Ames Division, Miles Labs, p. 28–32 (1976).
"Serum Protein Abnormalities Diagnostic and Clinical Aspects", Ritzmann and Daniels, eds., Little Brown and Company, First Edition, p. 314–330 (1975).
Miller et al., Clin, Chem., vol. 30, p. 1467–72 (1984).
Berson et al., *Methods in Investigative and Diagnostic Endocrinology* p. 111–116 (1973).
Berson et al., *Methods in Investigative and Diagnostic Endocrinology* p. 169–177 (1973).
Ekins, Nature, vol. 284, p. 14–15 (Mar. 6, 1980).
Ekins, Nature, vol. 340, pp. 256–258 (Jul. 27, 1989).
Ekins State of the Art, and Perspectives of Immunoassay, *International Symposium on Molecular Proves: Technology and Medical Applications* (Florence, Apr. 11–13, 1988).
Ekins, *Towards Immunoassays of Greater Sensitivity, Spefificity and Speed: An Overview*, Elsevier/North–Holland Biomedical Press, pp. 3–21 (1981).—Including commercially–available free hormone assays cited therein.
Graff, A Handbook of Routine Urinanalysis, Philadelphia: J.B. Limpincott Company (1983).
Giraudl, Analytica Chimica Acta, vol. 381:133–146 (1999).
Miles et al., *J. Biol. Chem.*, vol. 258, No. 23, pp. 12545–12552 (1981).
Rordorf et al., *J. Immunological Methods*, vol. 59, pp. 105–112 (1983).
Benton et al., *Science*, vol. 196, pp. 180–182 (1977).
Maniatis et al., Molecular Cloning: A Laboratory Manual (1982).
Southern, *J. Mol. Biol.*, vol. 98, p. 503 (1975).
St. John, T.P. et al., *Cell*, vol. 16, p. 443 (1979).
St. John, T.P., The Organization and Transcription of the *Saccharomyces Cerevisiae* Galactose Gene Cluster, A Dissertation Submitted to the Department of Biochemistry and the Committee on Graduate Studies of Stanford University in Partial Fulfillment of the Requirements For the Degree of Doctor of Philosophy (May 1980).
"Plaintiff Affymetrix's Preliminary Invalidity Contentions, Identification of Prior Art, and Accompanying Document Production Pursuant to Patent L.R. 3–3 and 3–4".
"Third Amended Complaint for Declaratory Judgement—Demand for July Trial".
Request for Reexamination of U.S. Patent No. 5,432,099 filed by Affymetrix on Mar. 19, 2004.
Bright & Appleby, J Biol Chem, vol. 244:3625 (1969).
Brown, Clin Chem, vol. 31: 1500–01 (1985).
Masouredis, J Lab Clin Med, vol. 110(3):308–17 (1987).

Jackola et al., "Variable binding affinities for allergen suggest a 'selective competition' among immunoglobulins in atopic and non–atopic humans", In: Mol Immunol, vol. 39(5–6): 367–77 (2002).
Munns et al., Biochemistry, vol. 28: 10048–54 (1989).
Lopez, Rev Fr Transfus, Immunochematol, vol. 19(1): 117–26 (1976).
Shipolini, R, In: FEBS Letters, vol. 17:39–40 (1971).
Shons et al., J Biomed Matter Res. vol. 6: 565–569 (1972).
Underwood, J of Immunol Meth, vol. 164: 119–130 (1993).
Romano et al., Vox Sang, vol. 45(5):378–83 (1983).
Weber, In: Allergy, vol. 42:464–70 (1987).
Translation of Multilyte's response in 'Case 9' filed with the Federal Patent Court on Feb. 9, 2004; Official File No. 3 Ni 39/03 (EU); Patent: EP 304 202; H–E File: 100779/u8; pp. 1–35.
T.A. Wilkins et al., "Comprehensive study of a thyroxin–analog–based assay for free thyroxin", Clin. Chem., vol. 31, No. 10, Oct. 1985, pp. 1644–1653.
[Proposed ] Fourth Amended Complaint for Declaratory Judgement—Demand for Jury Trial.
Conway et al, Quantitative Slide Micro–Immunoenzymatic Assay (Micro–SIA) for Antibodies to Particulate and Non–Particulate Antigens, Journal of Immunological Methods, 59 (1983) 39–47. Elsevier Biological Press.
Conway et al, Slilde Immunoenzymatic Assay (SIA) in Hybridoma Technology, Methods in Enzymology, vol. 121, Academic–Press 1986, 509–525.
Ekins, Assay Design and Quality Control, 1979 Elsevier/North–Holland Biomedical Press, 239–255.
Ekins, Current Concepts and Future Developments, Altenative Immunoassays, Chapter 13, 1985 John Wiley & Sons, Ltd., 219–237.
Finckh et al, Microspot—an ultrasensitive microarray–based ligand assay system. A practical application of ambient analyte assay theory, Prod UK NEQAS Meeting 1998: 155–165.
Gallo et al, Multiple–Antigen Slide Test for Detection of Immunoglobulin M Antibodies in Newborn and Infant Sera by Immunofluorescence, Journal of Clinical Microbiology, Apr. 1981, 631–636.
Hughes–Jones, Fuctional Affinity Constants of the Reaction Between 1 2 5 I–Labeled C1q and C1q Binders and their Use in the Measurement of Plasma C1q Concentrations, Immunology 1977, 32, 191–198.
Miller et al, Application of the MAST Immunodiagnostic System to the Determination of Allergen–Specific Ig–E, Clin. Chem. 30/9, 1984, 1467–1472.
Rej, et al, Direct Immunological Determination of Aspartate Aminotransferase Isoenzymes, Clin. Chem. 27/9 (1981), 1597–1601.
Wang, A Micro Immunofluorescence Method. Study of Antibody Response to TRIC Organisms in Mice, Trachoma and Related Disorders Caused by Clamydial Agents, Proceeding of a Symposium held in Boston, Massachusetts, Aug. 17–20, 1970, 273–288.
Wines et al, Enhancement of the Binding of C1q to Immune Complexes by Polyethylene Glycol, Molecular Immunology, vol. 25, No. 3, 1988, 263–266.
Translation of Multylite's Response in "Case 9" filed with the Federal Patent Court on Feb. 9, 2004.
Translation of Multylite's Response in "Case 3" filed with the Federal Patent Court on Feb. 9, 2004.

Translation of the Brief Submitted to the Federal Patent Court on Jun. 24, 2004.
Translation of Multylite' response in case 426/03 to Affymetrix'rejoinder dated Mar. 12, 2004.
Translation of Multylite's response in case 0268/03 to Affymetrix' rejoinder dated Mar. 12, 2004.
Order from High Court of Justice Chancery Division Patents Court revoking European Patent (UK) No. 0134215 and European Patent (UK) No. 0304202.
Multylite's Opening Claim Construction Brief on Case No.: C–03–3779 WHA.
Edwin F. Ullman, Curriculum Vitae.
Von Menges, Declaration on Reexamination of US Patent 5,432,099*.
Multilyte's Request for Reexamination of USP 5,432,099 of Nov. 10, 2003.
Merriam–Webster OnLine Dictionary, definition of word "insignificant".
Bright & Appleby, J Biol Chem, vol. 244: 3625 (1969).
Brown, Clin Chem, vol. 31:1500–01 (1985).
Conway de Macario et al., Jounal of Immunol. Meth, vol. 59: 39–47 (1983).
Current concepts and Future Developments in Alternative Immunoassays, Collins ed., John Wiley & Sons, (1985).
Dissanayake et al., Immunology, vol. 32(3): 309–18 (1977).
Ekins et al., In: Alternative Immunoassays, Collins Ed., NY: John Wiley & Sons, Chapter 13 (1985).

Graff, In: A Handbook of Routine Urinalysis, Philadelphia: J.B. Lippincott Company (1983).
Giraudi, Analytica Chimica Acta, vol. 381:133–146 (1999).
Gordon et al., "A Multidot Immunobinding Assay for Autoimmunity and the Demonstration of Novel Antibodies against Retroviral Antigens in the Sera of MRL Mice", In: J. Immunol Methods, vol. 59: 105–112 (1983).
Hawkes et al., Anal Biochem, vol. 119: 142 (1982).
J Lab Clin Med, vol. 110(3): 308–17 (1987).
Litman and Ullman, Clin Chem, pp. 1598–1603 (1983).
Miller et al., In: Clin Chem, vol. 30(9):1467–1472 (1984).
Modern Urine Chemistry: A Guide to the Diagnosis of Urinary Tract Diseases and Metabolic Disorders, Ames Division, Miles Laboratories Inc (1976).
Rev Fr Transfus, Immunohematol, vol. 19(1): 117–26 (1976).
Serum Protein Abnormalities, Diagnostics and Clinical Aspects, Ritzmann and Daniels, eds., Little, Brown & Co., p. 534 (1975).
Vonderviszt et al., Biochem J, vol. 243(2); 449–55 (1987).
Vox Sang, vol. 45(5): 378–83 (1983).
Expert Declaration, Dr. Edwin F. Ullman, dated Oct. 14, 2003, 24 pages.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–17 is confirmed.

* * * * *